US006391886B1

(12) United States Patent
Lee

(10) Patent No.: US 6,391,886 B1
(45) Date of Patent: May 21, 2002

(54) ORAL COMPOSITIONS HAVING IMPROVED CONSUMER AESTHETICS

(75) Inventor: Kuo-Chung Mark Lee, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/729,406

(22) Filed: Dec. 4, 2000

(51) Int. Cl.$^7$ .......................... A01N 43/42; A61K 31/44
(52) U.S. Cl. ........................................ 514/289; 514/570
(58) Field of Search ................................. 514/570, 289

(56) References Cited

U.S. PATENT DOCUMENTS

| | | | |
|---|---|---|---|
| 4,032,661 A | 6/1977 | Rowsell et al. | |
| 4,136,163 A | 1/1979 | Watson et al. | |
| 4,459,425 A | 7/1984 | Amano et al. | |
| 4,822,597 A | 4/1989 | Faust et al. | |
| 4,853,212 A | 8/1989 | Faust et al. | |
| 5,009,893 A | * 4/1991 | Cherukuri | 424/440 |
| 5,196,436 A | * 3/1993 | Smith | 514/289 |
| 5,451,404 A | 9/1995 | Furman | |
| 5,725,865 A | 3/1998 | Mane et al. | |
| 5,766,622 A | * 6/1998 | Nelson | 424/440 |
| 5,843,466 A | 12/1998 | Mane et al. | |

FOREIGN PATENT DOCUMENTS

| | | |
|---|---|---|
| JP | 12-273050 A | 10/2000 |
| WO | WO96/23486 A1 | 8/1996 |
| WO | WO98/52545 A1 | 11/1998 |

OTHER PUBLICATIONS

Basic and Clinical Pharmacology, Bertram G. Katzung, Appleton and Lange p. 33 (1995).*
Catterall et al., "Local Anesthetics", *Goodman & Gilman's The Pharmacological Basis of Therapeutics*, Chapter 15, pp. 331–347, 9$^{th}$ Edition, McGraw–Hill (1996).
Kandel et al., "The Bodily Senses", *Principles of Neuroscience*, 4$^{th}$ Edition, pp. 441–443, 2000.

* cited by examiner

*Primary Examiner*—Gary Geist
*Assistant Examiner*—Zachary Tucker
(74) *Attorney, Agent, or Firm*—Joan B. Cunningham; John M. Howell; Karen F. Clark

(57) ABSTRACT

Oral compositions containing therapeutical agents wherein the undesirable consumer aesthetics associated with these agents are mitigated using coolants and sweeteners.

17 Claims, No Drawings

007
ORAL COMPOSITIONS HAVING IMPROVED CONSUMER AESTHETICS

TECHNICAL FIELD

The present invention is for oral compositions containing therapeutic agents that generally have undesirable consumer aesthetics. Such compositions include compositions in a variety forms including liquids and solids comprising pharmaceutical actives. The liquid compositions include, but are not necessarily limited to elixirs, syrups, liquid-filled chewable capsules, suspensions, sprays, and suspensions.

BACKGROUND OF THE INVENTION

Stimulation of the nerves in the mouth takes place when flavors or chemical substances are readily available to stimulate these nerves. Oral compositions containing therapeutic agents such as pharmaceutical actives frequently contain disagreeable tasting or unpalatable components. These compositions are taken by mouth and frequently are designed to deliver the agent into the blood through the mucosa of the intestinal tract. These formulations are not intended to deliver their therapeutic agents through the mucosa of the mouth and esophagus. Such compositions are made to taste as good as possible in order to improve the patient compliance. This is usually done by using a sufficient level of sugar/syrup and, or sweeteners, and flavors to mask negative product taste. The medicines may optionally be administered in a volume wherein the therapeutic agent is diluted sufficiently to avoid the poor taste of such.

It is possible, however, to prepare formulations that are intended to deliver substantial portions of the therapeutic agent through the intra-oral mucosa. One problem associated with doing this is that the therapeutic agents can cause very strong negative sensory perceptions in the mouth due to their delivery through the mucosa. These perceptions are undesirable and are often so objectionable that a patient stops taking the medicine that might otherwise give them a desired health benefit. In such cases, the use of conventional sweetener/flavor approach is not sufficient to mask or hide these negative perceptions.

Sweeteners and coolants, both are sufficiently well known for use in medicines for improving consumer acceptance. For example, U.S. Pat. Nos. 4,822,597 and 4,853,212, both to Faust, issued 4/18/89 and 8/1/89 respectively, disclose chewing gums delivering anesthetics to numb irritated areas of the throat; incorporated herein by reference. These patents disclose peppermint and menthol and water-soluble sweeteners, extractable sweeteners and, or artificial sweeteners. U.S. Pat. Nos. 5,725,865 and 5,843,466, both to Mane, issued 3/10/98 and 12/1/98 respectively, disclose coolant compositions comprising mono menthyl succinate and its salts intended to mitigate bitterness attributable to known coolant compounds. Such compositions utilize flavoring syrups containing the natural sugar sorbitol; incorporated herein by reference. U.S. Pat. No. 5,009,893, Cherukuri et al, issued 4/23/91 discloses using menthol in combination with N-substituted p-methanecarboxamide compounds as coolant compositions in edible products; incorporated herein by reference. U.S. Pat. No. 5,451,404, Furman, issued Sep. 19, 1995 discloses coolant compositions comprising a ketal and a secondary coolant that are useful in toiletry foodstuffs, beverages or tobacco compositions; incorporated herein by reference.

Compositions containing therapeutic agents that are formulated to be absorbed through the oral mucosal tissue can produce strong irritation. Irritation as discussed in this application is defined as a singular or combined perceived sensations produced upon the therapeutic agent in sufficient concentration contacting the oral mucosal tissues. These sensations include prickling of the tissue similar to that experienced when the tongue comes into contact with sharp flavors or highly carbonated liquids such as club soda. Additionally irritation as used herein includes the non-thermally generated burning sensation upon contacting mucosal tissue. An example of the burning sensation is the sensation upon eating hot peppers or consuming liquors containing a high level of alcohol. Finally as used herein, irritation includes a tissue-numbing sensation. By tissue-numbing, or simply "numbing", it is meant that there is an absence of feeling much like that when oil of cloves is applied to a sore area of the mouth.

The levels of sweetener and coolant as normally used in the art will not generally provide enough relief of bitterness associated with the agent and the objectionable irritation mentioned above. When used in levels high enough to combat the bitterness attributed to such agents, the sweeteners themselves impart a bitter, metallic or other objectionable taste to the composition. If the coolant level is raised to levels high enough to combat the irritation caused by the agent, a burning sensation often results. There remains a need then to develop formulations that while delivering actives for oral mucosal absorption strong negative local effects are significantly reduced.

SUMMARY OF THE INVENTION

The present invention is for oral compositions comprising therapeutic agents, particularly those intended to be primarily delivered through oral mucosal tissue. These compositions comprise a combination of sweeteners and coolants wherein the irritation association with the composition's therapeutic agent or agents contacting mucosal tissue is substantially mitigated. Surprisingly it has been discovered that through there is a synergistic effect using high levels of both sweetening agents or sweeteners and cooling agents or coolants, both being undesirable when used alone at the levels attributed to the combination of the present invention. Mitigating irritation attributed with the therapeutic agent while creating compositions that taste good improves patient or user compliance to prescribed or recommended therapies that include consumption of such therapeutic agents.

DETAILED DESCRIPTION OF THE INVENTION

It is known to those skilled in the art that sweeteners, particularly artificial sweeteners used at high levels result in the composition having a bitter, metallic or other objectionable. Likewise coolants at high levels high result in the composition producing other forms of irritation such as burning, or headaches similar to those when eating frozen dessert such as ice cream or consuming highly iced beverages such as shushes. One skilled in the art would expect that using high levels of both coolant and sweeteners to mitigate the negatives associated with therapeutic agents would not produce a consumer-desirable composition. Surprisingly, however, when these components are combined in a composition containing therapeutic agents, there is a dramatic improvement in terms of the consumer-noticeable aspects of such a composition. The irritation of the mucosal tissue due primarily to the therapeutic agent including burning, prickly feel, numbing and other penetrating effects are dramatically reduced to a point wherein the consumer does not find such a composition objectionable. There is very little or no perceptible bitter, metallic or other objectionable taste associated with the sweetener and, or coolants.

Therapeutic Agents

Without being restricted to theory, the applicants believe that at high concentrations, the therapeutic agents delivered to the oral mucosal membranes lead to activation of a number of non-specific afferent neural pathways leading to the brain. Inducing histamine release from mast cells within the mucosal membranes are thought to induces sensations that include burning, prickling and itching of the oral tissue in the mouth. These histamines and other neurotransmitters, or the therapeutic agent itself may cause a large stimulation of the nerve fibers called nociceptors (or pain receptors) within the mucosal membranes. This results in chemical burning pain. Nociceptors and pain sensation are described in *Principles of Neuroscience*, E. R. Kandel, J. H. Schwartz, T. M. Jessel editors, p. 442, McGraw Hill, 4$^{th}$ edition, 2000; herein incorporated by reference. The bitter nature of the therapeutic agents in compositions of the present invention induce stronger than normal stimulation of the taste buds. The sensations of taste, including bitterness, salty, sour, and sweetness, as well as the sensation of pain, travel to the brain through numerous nerve pathways. When numerous pathways are stimulated at once with therapeutic agents at high levels, the result sensations experienced may be completely overwhelming. Thus when compositions comprising therapeutic agents capable of being delivered through the oral mucosal are used, it is highly likely that overwhelming stimulation of sensory mechanisms within the mouth occurs. This is particularly the case since the concentration of therapeutic agents achieved within the oral mucosal tissues where the nerve endings are located may be from 10,000 to 100,000 times greater that that of the non-mucosal or conventional product forms intended to be swallowed.

A key aspect in relation to the therapeutic agents used in the present invention is the agent's mucosal delivery potential. This being the case, the invention has application to many numerous classes of therapeutic agents that may be delivered in such a manner. These classes of therapeutic agents include, but are not necessarily limited to those selected from the group consisting of divalent cations such as zinc, amino acids, alkaloids, local anesthetics, type 1 and 2 histamine antagonists, analgesics, anti-inflammatories, expectorants, mucolytics and mucus-modifying agents, anti-tussive agents, antimalarials, anti-migraine, asthma treatments, sympathomimetic agents, anti-epileptics, decongestants, antibiotics, anti-anginal agents, water soluble vitamins, fat soluble vitamins, agents for maintaining or restoring glucose homeostasis, steroid hormones, antivirals, anti-protozoal agents including anti-malarials, proton pump inhibitors, anti-emetics, anti-arrhythmics, opiods, anti-psychotic agents, sleep aids and mixtures thereof. The actives useful in the present invention are present at a level from about 0.075% to about 25.0%, alternatively from about 0.28% to 10.0% and from about 1.0% to about 3.0% by weight of the composition.

The invention is also useful for compositions comprising alone, or in combinations with, in free or addition salt form the following therapeutic agents: dextromethorphan, acetaminophen, ephedrine and pseudoephedrine, ibuprofen, ketoprofen, guaifenesin, ambroxol, bromhexine, diphenhydramine, chlorpheniramine, doxylamine, triprolidine, clemastine, dimenhydrinate, cetirizine and loratidine.

Sweetener and Coolant Combinations

The sweeteners and sweeteners combinations are specifically selected on their strength so as to extend their affect throughout the period wherein the agent causes perceptible irritation. The sweeteners of the present invention are used at high levels wherein if such sweeteners were used alone in the composition of the present invention, the composition would have an objectionable taste. In the case of the sweeteners, the total level of sweeteners found in compositions of the present invention are from about 0.40% to about 3.3% of the composition. Alternatively the level of sweetener is from about 1.2% to about 2.7% and from about 1.4% to about 2.0% of the composition. Sweeteners of the present invention are selected from the group consisting of sodium saccharine or 1,2-benzisothiazol-3(2H)-one 1,1-dioxide, available as Sweetmate® from The NutraSweet Company, potassium acesulfame or 6-methyl-1,2,3-oxathiazin-4(3H)-one 2,2-dioxide, available as Sunett® from Nutrinova Company, sucralose or 1',4,6'-trichloro-galactosucrose, available as Splenda® from McNeil Specialty Products Company, aspartame or N-L-alpha-aspartyl-L-phenylalanine 1-methyl ester, available as NutraSweet® or Equal® from The NutraSweet Company, monoammonium glycyrrhizinate, neohesperidin dihydrochalcone (NHDC), thaumatin, a basic protein extracted from the fruit of the tropical plant, *Thaumatocous danielli*, available as Talin® from The Talin Food Company, and mixtures thereof. In the present invention the following sweetener or groups of sweeteners at their levels in the composition may be used to optimize the composition's taste:

Group A: sucralose at a level from about 0.4% to about 2.0%;

Group B: sucralose at a level from about 0.4% to about 1.5% and from about 0.0001% to about 1.5% of a second sweetener selected from the group consisting of saccharin, acesulfame, aspartame and mixtures thereof;

Group C: sucralose at a level from about 0.0001% to about 1.5% and from about 0.8% to about 1.5% of a second sweetener selected from the group consisting of saccharin, acesulfame, aspartame and mixtures thereof;

Group D: from about 0.8% to about 1.5% of a sweetener selected from the group consisting of saccharin, acesulfame K, aspartame and mixtures thereof and from about 0.0001%) to about 0.30% of a second sweetener selected from the group consisting of monoammonium glycyrrhizinate, neohesperidin dihydrochalcone, thaumatin and mixtures thereof;

Group E: sucralose at a level from about 0.4% to about 2.0% and from about 0.0001% to about 0.30% of a second sweetener selected from the group consisting of monoammonium glycyrrhizinate, neohesperidin dihydrochalcone, thaumatin and mixtures thereof;

Group F: from about 0.4% to about 3.0% of the Group B sweetener and from about 0.0001% to about 0.30% of a second sweetener selected from the group consisting of monoammonium glycyrrhizinate, neohesperidin dihydrochalcone, thaumatin and mixtures thereof;

Group G: from about 0.8% to about 3.0% of the Group C sweetener and from about 0.0001% to about 0.30% of a second sweetener selected from the group consisting of monoammonium glycyrrhizinate, neohesperidin dihydrochalcone, thaumatin and mixtures thereof.

The coolants of the present invention include, but are not limited to the wide range of commercially sold coolants. In the case of the coolants, the total level of coolants found in compositions of the present invention are from about 0.25% to about 1.10% of the composition. Alternatively the level of coolants is from about 0.25% to about 0.80% and from about 0.30% to about 0.65% of the composition. Coolants of the present invention are selected from the group consisting of menthol, the class of carboxamides, preferably N-ethyl-p-menthane-3-carboxamide and N,2,3-trimethyl-2-isopropylbutanamide available as WS-3 and WS-23 respectively, both from Millennium Specialty Chemicals; 1-menthone-/d-iso-menthone glycerin ketal and menthyl lactate available as MGA and Frescolt® respectively from Haarmann and Reimer; 3-1-menthoxypropane-1,2-diol available as TK-10® from Takasago Perfumery Co., Tokyo, Japan, menthyl acetoacetate available as Novillone® from Noville, mono menthyl succinate available as Physcool® from Mane and Optacool® from Haarmann and Reimer, and Coolant 3, Coolant 4 & Coolant 5, from International Flavors & Fragrances. In the present invention the following coolant or groups of coolants at their levels in the composition may be used to optimize the composition's taste:

Group 1: from about 0.1% to about 0.4% menthol and from about 0.1% to about 0.4% WS-3 wherein the minimum level of the combination is 0.25% of the composition;

Group 2: from about 0.1% to about 0.3% menthol and from about 0.1% to about 0.3% WS-3 and from about 0.05% to about 0.40% MGA;

Group 3: from about 0.15% to about 0.4% menthol and from about 0.1% to about 0.40 MGA;

Group 4: from about 0.15% to about 0.4% WS-3 and from about 0.1% to about 0.4% MGA;

Group 5: from about 0.25% to about 0.80% of a coolant selected from any individual Group 1, 2, 3 and 4 and from about 0.0001% to about 0.3% of a coolant selected from the group consisting of WS-23, TK-10, Optacool, Physcool, IFF Coolants and mixtures thereof.

In the present invention, when sweeteners from Groups A through G are combined with coolants from Groups 1 through 5 provide significantly mitigation of irritation resulting from the therapeutic agents in the composition while providing good taste.

Additional Ingredients

There are a number of additional ingredients that are used for making the compositions of the present invention in the desired product forms including liquids. Such ingredients are found in co-pending PCT patent applications including WO00/00575, WO00/41694 and WO00/41692, all published Jul. 20, 2000, all assigned to Procter and Gamble and all herein incorporated by reference.

In the case of liquid compositions of the present invention, poloxyalkelene block copolymer or "poloxamers" are very useful in creating pourable liquids that gel upon contact with the wet mucosal tissues in the mouth and throat. Such materials are disclosed in pending U.S. patent application Ser. No. 09/658813, filed Sep. 11, 2000, assigned to Procter & Gamble, herein incorporated by reference.

Other specific additional ingredients that are used for making the compositions of the present invention in desired product forms include hydrophilic solvents. The solvent portion of compositions of the present invention comprises from about 60% to about 99.975%, preferably from 70% to about 99% and most preferably from about 85% to about 98% by weight of the composition.

The solvent of the present invention is normally liquid at ambient or room temperatures. It is water-soluble or water-miscible. Solvents of the present invention are preferably selected from the group consisting of propylene glycol, ethanol, poly(ethylene glycol) or PEG, propylene carbonate, diethylene glycol monoethyl ether, poloxamer, glycofurol, glycerol, and mixtures thereof. Propylene glycol and ethanol are particularly preferred, There are mixtures of these solvents that are particularly preferred for certain product forms of the present invention. For example, if the product form is an elixir, liquid capsule or liquid containing lozenge, the solvent is a combination of propylene glycol, ethanol, and PEG. If the product form is a spray, the solvent is a combination of propylene glycol, ethanol, PEG and usually propylene carbonate. The level of each solvent that makes up these mixtures is partially dependent on aesthetic benefits sought by the formulator. Most preferable are anhydrous forms of the above solvents.

EXAMPLES

Example I

Cough Treatment Composition

| Component | % (w/w) |
| --- | --- |
| Dextromethorphan Base | 2.20 |
| Propylene Glycol | 42.45 |
| Poloxymer[1] | 29.71 |
| Purified Water | 12.08 |
| Ethanol (100% w/w) | 10.91 |
| Sodium Metabisulphite | 0.10 |
| Disodium EDTA | 0.10 |
| Eucalyptus Flavor | 0.45 |
| Coolants: | — |
| Menthol | 0.20 |
| n-Ethyl p-mentha-3-carboxamide[2] | 0.15 |
| 1-Menthone-/d-iso-menthone glycerin ketal[3] | 0.30 |
| 3-1-Menthoxypropane-1,2-diol[4] | 0.10 |
| Sweeteners: | — |
| Sodium Saccharin | 0.60 |
| Potassium Acesulfame | 0.50 |
| Monoammonium Glycyrrhizinate | 0.15 |

[1]Pluronic F127 available from BASF Specialty Chemicals, Mount Olive, N.J.
[2]WS-3 available from Millennium Specialty Chemicals.
[3]MGA available from Haarmann and Reimer.
[4]TK-10 available from Takasago Perfumery Co., Tokyo, Japan.

Preparation:

Prepare an alcohol premix by adding Dextromethorphan Base, Monoammonium Glycyrrhizinate, Menthol, WS-3, TK-10 and MGA into a clean vessel. Add Ethanol and mix until clear and uniform.

In a separate vessel, prepare a water premix by adding together Disodium EDTA, Sodium Metabisulphite, Sodium Saccharin, and Potassium Acesulfame. Add Water and mix until homogenous.

Prepare the cough treatment composition by adding Propylene Glycol and F127 into a clean main vessel. Heat with mixing the combination to about 50° C. Cool the combination to about 35° C., and add with mixing the Alcohol Premix. Add with mixing the Water Premix to main vessel. Add Eucalyptus Flavor to main vessel and mix until homogenous.

Example II

Cough Treatment Composition

| Component | % (w/w) |
| --- | --- |
| Dextromethorphan Base | 2.75 |
| Propylene Glycol | 79.41 |
| Ethanol (100% w./w.) | 10.00 |
| Purified Water | 5.00 |
| Sodium Metabisulphite | 0.10 |
| Disodium EDTA | 0.10 |
| Artificial Orange Flavor | 0.50 |
| Coolants: | — |
| Menthol | 0.10 |
| n-Ethyl p-menthane-3-carboxamide[1] | 0.12 |
| 1-Menthone-/d-iso-menthone glycerin ketal[2] | 0.10 |
| Sweeteners: | — |
| 1',4,6'-Trichloro-galactosucrose[3] | 1.20 |
| Sodium Saccharin | 0.20 |
| Potassium Acesulfame | 0.40 |
| Monoammonium Glycyrrhizinate | 0.02 |

[1]WS-3 available from Millennium Specialty Chemicals.
[2]MGA available from Haarmann and Reimer.
[3]Sucralose, also known also as Splenda ™ available from McNeil Specialty Products Co.

Preparation:

Add into a clean vessel Dextromethorphan Base, Sodium Metabisulphite, Disodium EDTA, Sucralose, Sodium Saccharin, Potassium Acesulfame, Monoammonium Glycyrrhizinate, Menthol, WS-3 and MGA. Add Ethanol and then the Propylene Glycol and Water. Mix until clear and uniform. Add Artificial Orange Flavor and mix until clear and uniform.

Example III

Cough Treatment Composition

| Component | % (w/w) |
| --- | --- |
| Dextromethorphan Base | 1.69 |
| Propylene Glycol | 42.58 |
| Poloxymer[1] | 29.80 |
| Purified Water | 12.77 |
| Ethanol (100% w/w) | 10.91 |
| Sodium Metabisulphite | 0.10 |
| Disodium EDTA | 0.10 |
| Artificial Grape Flavor | 0.55 |
| Coolants: | — |
| Menthol | 0.10 |
| n-Ethyl p-menthane-3-carboxamide[2] | 0.15 |
| 1-Menthone-/d-iso-menthone glycerin ketal[3] | 0.25 |
| Sweeteners: | — |
| 1',4,6'-Trichloro-galactosucrose[4] | 0.80 |
| Potassium Acesulfame | 0.20 |

[1]Pluronic F127: BASF Specialty Chemicals, Mount Olive, N.J.
[2]WS-3 available from Millennium Specialty Chemicals.
[3]MGA available from Haarmann and Reimer.
[4]Sucralose also known also as Splenda ™ available from McNeil Specialty Products Co.

Preparation:

Prepare an alcohol premix by adding Dextromethorphan Base, Menthol, WS-3, and MGA into a clean vessel. Add Ethanol and mix until clear and uniform.

In a separate vessel, prepare a water premix by adding together Disodium EDTA, Sodium Metabisulphite, Sucrolose, and Potassium Acesulfame. Add Water and mix until homogenous.

Prepare the cough treatment composition by adding Propylene Glycol and F127 into a clean main vessel. Heat with mixing the combination to about 50° C. Cool the combination to about 35° C., and add with mixing the Alcohol Premix. Add with mixing the Water Premix to main vessel. Add Artificial Grape Flavor to main vessel and mix until homogenous.

Example IV

Cough Treatment Composition

| Component | % (w/w) |
| --- | --- |
| Dextromethorphan Base | 2.20 |
| Proplene Glycol | 42.45 |
| Poloxymer[1] | 29.71 |
| Purified Water | 12.08 |
| Ethanol (100% w/w) | 10.96 |
| Sodium Metabisulphite | 0.10 |
| Disodium EDTA | 0.10 |
| Eucalyptus Flavor | 0.65 |
| Coolants: | — |
| n-Ethyl p-menthane-3-carboxamide[2] | 0.20 |
| 1-Menthone-/d-iso-menthone glycerin ketal[3] | 0.30 |
| Sweeteners: | — |
| Sucralose[4] | 1.10 |
| Monoammonium Glycyrrhizinate | 0.15 |

[1]Pluronic F127 available from BASF Specialty Chemicals, Mount Olive, N.J.
[2]WS-3 available from Millennium Specialty Chemicals.
[3]MGA available from Haannann and Reimer.
[4]Sucralose: 1',4,6'-Trichloro-galactosucrose, known also as Splenda ™ available from McNeil Specialty Products Co.

Preparation:

Prepare an alcohol premix by adding Dextromethorphan Base, Monoammonium Glycyrrhizinate, WS-3, and MGA into a clean vessel. Add Ethanol and mix until clear and uniform.

In a separate vessel, prepare a water premix by adding together Disodium EDTA, Sodium Metabisulphite, and Sucralose. Add Water and mix until homogenous.

Prepare the cough treatment composition by adding Propylene Glycol and F127 into a clean main vessel. Heat with mixing the combination to about 50° C. Cool the combination to about 35° C., and add with mixing the Alcohol Premix. Add with mixing the Water Premix to main vessel. Add Eucalyptus Flavor to main vessel and mix until homogenous.

Example V

Cough Treatment Composition

| Component | % (w/w) |
| --- | --- |
| Dextromethorphan Base | 2.75 |
| Propylene Glycol | 79.80 |
| Ethanol (100% w./w.) | 10.00 |
| Purified Water | 5.00 |
| Sodium Metabisulphite | 0.10 |
| Disodium EDTA | 0.10 |
| Artificial Orange Flavor | 0.50 |

-continued

| Component | % (w/w) |
|---|---|
| Coolants: | |
| Menthol | 0.25 |
| 1-Menthone-/d-iso-menthone glycerin ketal[1] | 0.20 |
| Sweeteners: | |
| Sucralose[2] | 1.30 |

[1]MGA available from Haarmann and Reimer.
[2]Sucralose: 1',4,6'-Trichloro-galactosucrose, known also as Splenda ™ available from McNeil Specialty Products Co.

Preparation:

Add the Dextromethorphan Base, Sodium Metabisulphite, Disodium EDTA, Sucralose, Menthol and MGA into a clean vessel. Add Ethanol and then the Propylene Glycol and Water. Mix until clear and uniform. Add Artificial Orange Flavor and mix until clear and uniform.

Example VI

Composition for the Treatment of Cough

| Component | % (w/w) |
|---|---|
| Dextromethorphan Base | 1.69 |
| Propylene Glycol | 42.58 |
| Poloxymer[1] | 29.80 |
| Purified Water | 12.77 |
| Ethanol (100% w/w) | 10.66 |
| Sodium Metabisulphite | 0.10 |
| Disodium EDTA | 0.10 |
| Artificial Grape Flavor | 0.55 |
| Coolants: | |
| Menthol | 0.20 |
| n-Ethyl p-menthane-3-carboxamide[2] | 0.15 |
| Sweeteners: | |
| Sucralose[3] | 0.30 |
| Potassium Acesulfame | 0.50 |
| Sodium Saccharin | 0.60 |

[1]Pluronic F127: BASF Specialty Chemicals, Mount Olive, N.J.
[2]WS-3 available from Millennium Specialty Chemicals.
[3]Sucralose: 1',4,6'-Trichloro-galactosucrose, known also as Splenda ™ available from McNeil Specialty Products Co.

Preparation:

Prepare an alcohol premix by adding Dextromethorphan Base, Menthol, and WS-3 into a clean vessel. Add Ethanol and mix until clear and uniform.

In a separate vessel, prepare a water premix by adding together Disodium EDTA, Sodium Metabisulphite, Sucralose, Sodium Saccharin, and Potassium Acesulfame. Add Water and mix until homogenous.

Prepare the cough treatment composition by adding Propylene Glycol and F127 into a clean main vessel. Heat with mixing the combination to about 50° C. Cool the combination to about 35° C., and add with mixing the Alcohol Premix. Add with mixing the Water Premix to main vessel. Add Artificial Grape Flavor to Main vessel and mix until homogenous.

Example VII

Cough Treatment Composition

| Component | % (w/w) |
|---|---|
| Dextromethorphan Base | 2.20 |
| Propylene Glycol | 42.45 |
| Poloxymer[1] | 29.71 |
| Purified Water | 12.08 |
| Ethanol (100% w/w) | 10.91 |
| Sodium Metabisulphite | 0.10 |
| Disodium EDTA | |
| Eucalyptus Flavor | 0.45 |
| Coolants: | — |
| Menthol | 0.20 |
| n-Ethyl p-menthane-3-carboxamide[2] | 0.15 |
| 1-Menthone-/d-iso-menthone glycerin ketal[3] | 0.30 |
| 3-1-Menthoxypropane-1,2-diol[4] | 0.10 |
| Sweeteners: | — |
| Sucralose[4] | 0.20 |
| Sodium Saccharin | 0.50 |
| Potassium Acesulfame | 0.45 |
| Monoammonium Glycyrrhizinate | 0.10 |

[1]Pluronic F127 available from BASF Specialty Chemicals, Mount Olive, N.J.
[2]WS-3 available from Millennium Specialty Chemicals.
[3]MGA available from Haannann and Reimer.
[4]TK-10 available from Takasago Perfumery Co., Tokyo, Japan.
[5]Sucralose: 1',4,6'-Trichloro-galactosucrose, known also as Splenda ™ available from McNeil Specialty Products Co.

Preparation:

Prepare an alcohol premix by adding Dextromethorphan Base, Monoammonium Glycyrrhizinate, Menthol, WS-3, TK-10 and MGA into a clean vessel. Add Ethanol and mix until clear and uniform.

In a separate vessel, prepare a water premix by adding together Disodium EDTA, Sodium Metabisulphite, Sucralose, Sodium Saccharin, and Potassium Acesulfame. Add Water and mix until homogenous.

Prepare the cough treatment composition by adding Propylene Glycol and F127 into a clean main vessel. Heat with mixing the combination to about 50° C. Cool the combination to about 35° C., and add with mixing the Alcohol Premix. Add with mixing the Water Premix to main vessel. Add Eucalyptus Flavor to main vessel and mix until homogenous.

What is claimed is:

1. An oral liquid composition comprising:
   (a) from about 0.075% to about 25.0% by weight of an oral mucosal tissue irritating therapeutic agent;
   (b) from about 0.4% to about 2.0% by weight of a sucralose sweetener;
   (c) from about 0.1% to about 0.4% by weight of menthol; and
   (d) from about 0.1% to about 0.4% by weight of N-ethyl-p-menthane-3-carboxamide;
   wherein the composition comprises the menthol and the N-ethyl-p-menthane-3-carboxamide at a combined minimum level of 0.25% by weight of the composition.

2. The oral liquid composition of claim 1, comprising:
   (a) from about 0.4% to about 1.5% by weight of sucralose;
   (b) from about 0.0001% to about 1.5% by weight of a second sweetener selected from the group consisting of saccharin, acesulfame, aspartame, and mixtures thereof;
   (c) from about 0.1% to about 0.3% by weight of menthol;

(d) from about 0.1% to about 0.3% by weight of N-ethyl-p-menthane-3-carboxamide; and (e) from about 0.05% to about 0.40% by weight of 1-menthone/d-iso-menthone glycerin ketal.

3. An oral liquid composition comprising:

(a) from about 0.075% to about 25.0% by weight of an oral mucosal tissue irritating therapeutic agent;

(b) from about 0.0001% to about 1.5% by weight of sucralose;

(c) from about 0.8% to about 1.5% by weight of a second sweetener selected from the group consisting of saccharin, acesulfame, aspartame, and mixtures thereof;

(d) from about 0.15% to about 0.4% by weight of menthol; and (e) from about 0.1% to about 0.40% by weight of 1-menthone-/d-iso-menthone glycerin ketal.

4. An oral liquid composition comprising:

(a) from about 0.075% to about 25.0% by weight of an oral mucosal tissue irritating therapeutic agent;

(b) from about 0.8% to about 1.5% by weight of a sweetener selected from the group consisting of saccharin, acesulfame, aspartame, and mixtures thereof;

(c) from about 0.0001% to about 0.30% by weight of a second sweetener selected from the group consisting of monoammonium glycyrrhizinate, neohesperidin, dihydrochalcone, thaumatin, and mixtures thereof;

(d) from about 0.15% to about 0.4% by weight of N-ethyl-p-menthane-3-carboxamide; and (e) from about 0.1% to about 0.4% by weight of 1-menthone-/d-iso-menthone glycerin ketal.

5. The oral liquid composition of claim 1 further comprising from about 0.0001% to about 0.30% by weight of a second sweetener selected from the group consisting of monoammonium glycyrrhizinate, neohesperidin, dihydrochalcone, thaumatin, and mixtures thereof.

6. An oral liquid composition comprising:

(a) from about 0.075% to about 25.0% by weight of an oral mucosal tissue irritating therapeutic agent selected from the group consisting of dextromethorphan, a salt thereof, and mixtures thereof;

(b) from about 0.4% to about 2.0% by weight of a sucralose sweetener;

(c) from about 0.1% to about 0.4% by weight of menthol; and (d) from about 0.1% to about 0.4% by weight of N-ethyl-p-menthane-3-carboxamide;

wherein the composition comprises the menthol and the N-ethyl-p-menthane-3-carboxamide at a combined minimum level of 0.25% by weight of the composition.

7. The oral liquid composition of claim 6 comprising:

(a) from about 0.4% to about 1.5% by weight of sucralose;

(b) from about 0.0001% to about 1.5% by weight of a second sweetener selected from the group consisting of saccharin, acesulfame, aspartame, and mixtures thereof;

(c) from about 0.1% to about 0.3% by weight of menthol;

(d) from about 0.1% to about 0.3% by weight of N-ethyl-p-menthane-3-carboxamide; and (e) from about 0.05% to about 0.40% by weight of 1-menthone-/d-iso-menthone glycerin ketal.

8. An oral liquid composition comprising;

(a) from about 0.075% to about 25.0% by weight of an oral mucosal tissue irritating therapeutic agent selected from the group consisting of dextromethorphan, a salt thereof, and mixtures thereof;

(b) from about 0.0001% to about 1.5% by weight of sucralose;

(c) from about 0.8% to about 1.5% by weight of a second sweetener selected from the group consisting of saccharin, acesulfame, aspartame, and mixtures thereof;

(d) from about 0.15% to about 0.4% by weight of menthol; and (e) from about 0.1% to about 0.40% by weight of 1-menthone-/d-iso-menthone glycerin ketal.

9. An oral liquid composition comprising;

(a) from about 0.075% to about 25.0% by weight of an oral mucosal tissue irritating therapeutic agent selected from the group consisting of dextromethorphan, a salt thereof, and mixtures thereof;

(b) from about 0.8% to about 1.5% by weight of a sweetener selected from the group consisting of saccharin, acesulfame, aspartame, and mixtures thereof;

(c) from about 00001% to about 0.30% by weight of a second sweetener selected from the group consisting of monoammonium glycyrrhizinate, neohesperidin, dihydrochalcone, thaumatin, and mixtures thereof;

(d) from about 0.15% to about 0.4% by weight of N-ethyl-p-menthane-3-carboxamide; and (e) from about 0.1% to about 0.4% by weight of 1-menthone-/d-iso-menthone glycerin ketal.

10. The oral liquid composition of claim 6 further comprising from about 0.0001% to about 0.30% by weight of a second sweetener selected from the group consisting of monoammonium glycyrrhizinate, neohesperidin, dihydrochalcone, thaumatin, and mixtures thereof.

11. The composition of claim 6 comprising from about 0.28% to about 10.0% by weight of the dextromethorphan therapeutic agent.

12. The composition of claim 6 comprising from about 1.0% to about 3.0% by weight of the dextromethorphan therapeutic agent.

13. The oral liquid composition of claim 1 wherein the oral mucosal tissue irritating therapeutic agent is selected from the group consisting of dextromethorphan, a dextromethorphan salt, acetaminophen, ephedrine, pseudoephedrine, ibuprofen, ketoprofen, guaifenesin, ambroxyl, bromhexine, diphenhydramine, chlorpheniramine, doxylamine, triprolidine, clemastine, dimenhydrinate, cetirizine, loratidine, and mixtures thereof.

14. The oral liquid composition of claim 3 wherein the oral mucosal tissue irritating therapeutic agent is selected from the group consisting of dextromethorphan, a dextromethorphan salt, acetaminophen, ephedrine, pseudoephedrine, ibuprofen, ketoprofen, guaifenesin, ambroxyl, bromhexine, diphenhydramine, chlorpheniramine, doxylamine, triprolidine, clemastine, dimenhydrinate, cetirizine, loratidine, and mixtures thereof.

15. The oral liquid composition of claim 4 wherein the oral mucosal tissue irritating therapeutic agent is selected from the group consisting of dextromethorphan, a dextromethorphan salt, acetaminophen, ephedrine, pseudoephedrine, ibuprofen, ketoprofen, guaifenesin, ambroxyl, bromhexine, diphenhydramine, chlorpheniramine, doxylamine, triprolidine, clemastine, dimenhydrinate, cetirizine, loratidine, and mixtures thereof.

16. The oral liquid composition of claim 1 further comprising a hydrophilic water-miscible anhydrous solvent selected from the group consisting of propylene glycol, ethanol, poloxamer, and mixtures thereof.

17. The oral liquid composition of claim 6 further comprising a hydrophilic water-miscible anhydrous solvent selected from the group consisting of propylene glycol, ethanol, poloxamer, and mixtures thereof.

* * * * *